United States Patent [19]

Smith et al.

[11] Patent Number: 5,502,239

[45] Date of Patent: Mar. 26, 1996

[54] PROCESS FOR RECOVERING DIMETHYL TEREPHTHALATE

[75] Inventors: Brad L. Smith; Gary E. Wilkins, both of Wilmington, N.C.

[73] Assignee: Hoechst Celanese Corporation, Somerville, N.J.

[21] Appl. No.: 512,244

[22] Filed: Aug. 7, 1995

[51] Int. Cl.$^6$ .................................................. C07C 67/48
[52] U.S. Cl. .................................................. 560/78
[58] Field of Search .................................................. 560/78

[56] References Cited

U.S. PATENT DOCUMENTS

| | | | |
|---|---|---|---|
| 2,884,443 | 4/1959 | Siggel et al. | 260/475 |
| 3,037,050 | 5/1962 | Heisenberg et al. | 260/475 |
| 3,148,208 | 9/1964 | Siggel et al. | 260/475 |
| 3,321,510 | 5/1967 | Lotz et al. | 260/475 |
| 3,488,298 | 1/1970 | Barkey et al. | 260/2.3 |
| 3,907,868 | 9/1975 | Currie et al. | 260/475 |
| 4,013,519 | 3/1977 | Hoppert et al. | 203/33 |
| 4,078,143 | 3/1978 | Malik et al. | 560/78 |
| 4,118,582 | 10/1978 | Walker | 560/96 |
| 4,163,860 | 8/1979 | Delattre et al. | 560/96 |
| 4,578,502 | 3/1986 | Cudmore | 560/79 |
| 5,051,528 | 9/1991 | Naujokas et al. | 560/78 |
| 5,414,106 | 5/1995 | Smith et al. | 560/78 |
| 5,414,107 | 5/1995 | Smith | 560/79 |

*Primary Examiner*—José G. Dees
*Assistant Examiner*—Samuel Barts
*Attorney, Agent, or Firm*—R. H. Hammer, III

[57] ABSTRACT

A process for recovering dimethyl terephthalate (DMT) comprises the steps of: providing a dimethyl terephthalate stream including dimethyl terephthalate, glycols, and coordination compounds; acidifying the coordination compounds to disassociate the ligands from the metalions; separating the ligands from the metalions; separating the dimethyl terephthalate from the glycols; and recovering the dimethyl terephthalate. Additionally, the process may include the step of basifying the metalions to precipitate the metal; and recovering the metal.

6 Claims, 3 Drawing Sheets

PROCESS FOR RECOVERING DIMETHYL TEREPHTHALATE

FIELD OF THE INVENTION

This invention is directed to the recovery of dimethyl terephthalate (DMT) from scrap polyethylene terephthalate (PET) and PET production waste; this process addresses the recovery of coordination compounds formed as a result of water being present during the methanolysis.

BACKGROUND OF THE INVENTION

Scrap polyethylene terephthalate (PET) and PET production waste are often landfilled. Landfilling of these materials represents, among other things, a loss of raw material, and a potential ecological problem, if improperly landfilled. Accordingly, an economical process for the recycling of these materials is desirable.

The recycling of scrap PET and PET production waste, in general, is known. These materials can be reacted with methanol, i.e., "methanolysis", to produce dimethyl terephthalate (DMT). For example, see: U.S. Pat. Nos. 2,884,443; 3,073,050; 3,148,208; 3,321,510; 3,488,298; 3,907,868; 4,163,860; 4,578,502; 5,051,528; 5,414,106; and 5,414,107. These materials, alternatively, can be reacted with ethylene glycol, i.e., "glycolysis", to produce bis-(2-hydroxyethyl) terephthalate (BHET), a PET monomer. For example, see: U.S. Pat. No. 4,078,143, column 1. Scrap PET can, also, be melted and reformed without depolymerization. Additionally, there are known methods by which catalyst can be removed from PET production waste. For example, see: U.S. Pat. Nos. 4,013,519 and 4,118,582.

One problem that arises during methanolysis, results from the use of methanol containing water (e.g., methanol containing greater than 0.5% by weight water). Due to the presence of water, monomethyl terephthalate (MMT) and/or terephthalatic acid (TA) can be formed during methanolysis. Much of this MMT and TA acts as ligands for the catalyst, especially the manganese and antimony catalysts present in the stream. The ligands and metals combined together are known as coordination compounds.

Much of the coordination compounds is purged from the recycle process along with the bottoms from the glycol stripper column of the recycle process (explained below). The loss of MMT and TA coordination compounds is a yield loss, when the entire recycle process is considered.

Additionally, the coordination compounds that are not removed by the stripper column can foul downstream processing equipment, such as reboilers. The coordination compounds that foul the equipment form a viscous and difficult to handle material. This material causes equipment down-time for cleaning, and thereby increases costs. Therefore, the effective recovery of the coordination compounds could produce yield improvements to the overall process, as well, lowering costs by decreasing down-time for equipment cleaning.

SUMMARY OF THE INVENTION

A process for recovering dimethyl terephthalate (DMT) comprises the steps of: providing a dimethyl terephthalate stream including dimethyl terephthalate, glycols, and coordination compounds; acidifying the coordination compounds to disassociate the ligands from the metal ions; separating the ligands from the metal ions; separating the dimethyl terephthalate from the glycols; and recovering the DMT. Additionally, the process may include the steps of basifying the metal ions to precipitate the metal; and recovering the metal.

BRIEF DESCRIPTION OF THE DRAWINGS

For the purpose of illustrating the invention, there is shown in the drawings forms of the invention which are presently preferred; it being understood, however, that this invention is not limited to the precise arrangements and instrumentalities shown.

DETAILED DESCRIPTION OF THE INVENTION

Figure 1:
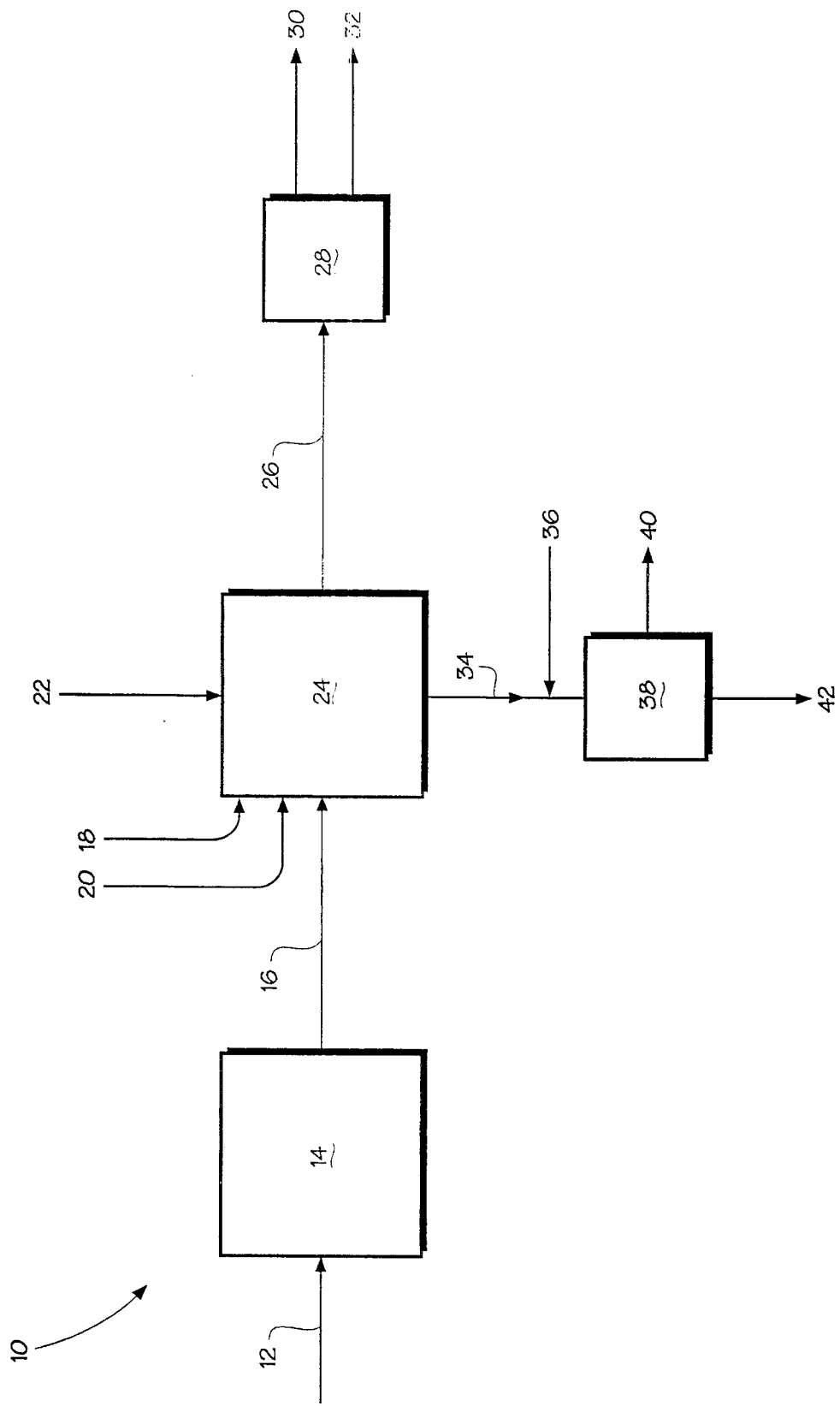
FIG. 1 is a flow diagram of the present invention.

The following is a detailed description of the invention, similar terms are used to describe the elements of the various embodiments shown in the drawings. The drawings are discussed below. A description of the terms follows the discussion of the drawings.

Referring to FIG. 1, there is shown a process 10 for the recovery of dimethyl terephthalate (DMT).

A waste stream 12 is fed into a methanolysis reactor 14. Methanolysis reactor 14 produces a DMT stream 16. Methanolysis reactor 14 preferably includes a methanol stripper (not shown) to remove methanol from DMT stream 16. This methanol may be recycled into reactor 14.

DMT stream 16, solvent 18, water 20, and acid 22 are fed into extractor 24. Therein, an organic phase 26 and an aqueous phase 34 are formed. Organic phase 26 is further processed in an organic phase separator 28 where the solvent 32, and the DMT and the ligands 30 are separated in any known manner. Optionally, but preferably, aqueous stream 34 may be treated with base stream 36 prior to filter 38, and the base precipitates out the metals 42 that are removed by filter 38. The water/glycol stream 40, produced from filter 38, may be resolved in any known manner, e.g. distillation.

Figure 2:
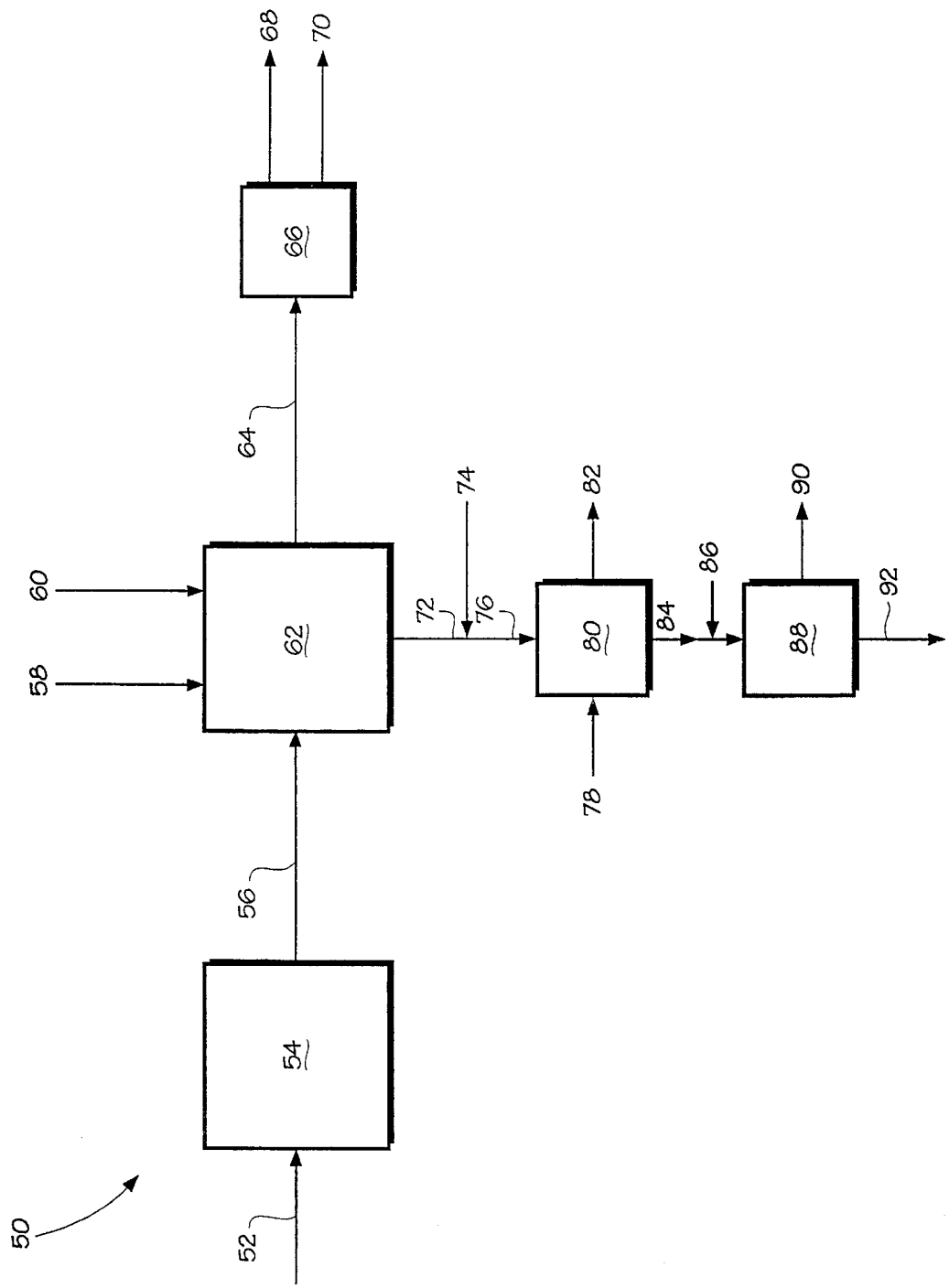
FIG. 2 is a flow diagram of an alternate embodiment of the present invention.

Referring to FIG. 2, an alternate process for recovering DMT 50 is shown.

Waste stream 52 is fed into methanolysis reactor 54 to produce DMT stream 56. DMT stream 56, solvent stream 58, and water stream 60 are fed into extractor 62. In extractor 62, an organic phase 64 and an aqueous phase 72 are formed. Organic phase 64 generally comprises solvent and DMT. Aqueous phase 72 generally comprises water, glycols, catalysts, and coordination compounds.

Organic phase 64 is fed into organic phase separator 66 were DMT 68 is separated from solvent 70 in a known manner.

Aqueous phase 72 is treated with acid stream 74. The resulting stream 76 contains water, glycols, catalysts, and ligands. Stream 76 and ligand extraction solvent 78 are fed into ligand extractor 80. The ligand extraction solvent may be the same as the foregoing solvent used in the extractor 62. The ligand extractor's 80 operation is the same in principal as extractor 62. In ligand extractor 80, a ligand/solvent phase 82 and an aqueous phase 84 (containing water, glycols, catalysts) are formed. Aqueous phase 84 is, preferably, treated with base stream 86 and fed into filter 88. In filter 88, water and glycols 90 are separated from metal 92. Water and glycols 90 may be resolved in any known manner, e.g. distillation.

Figure 3:
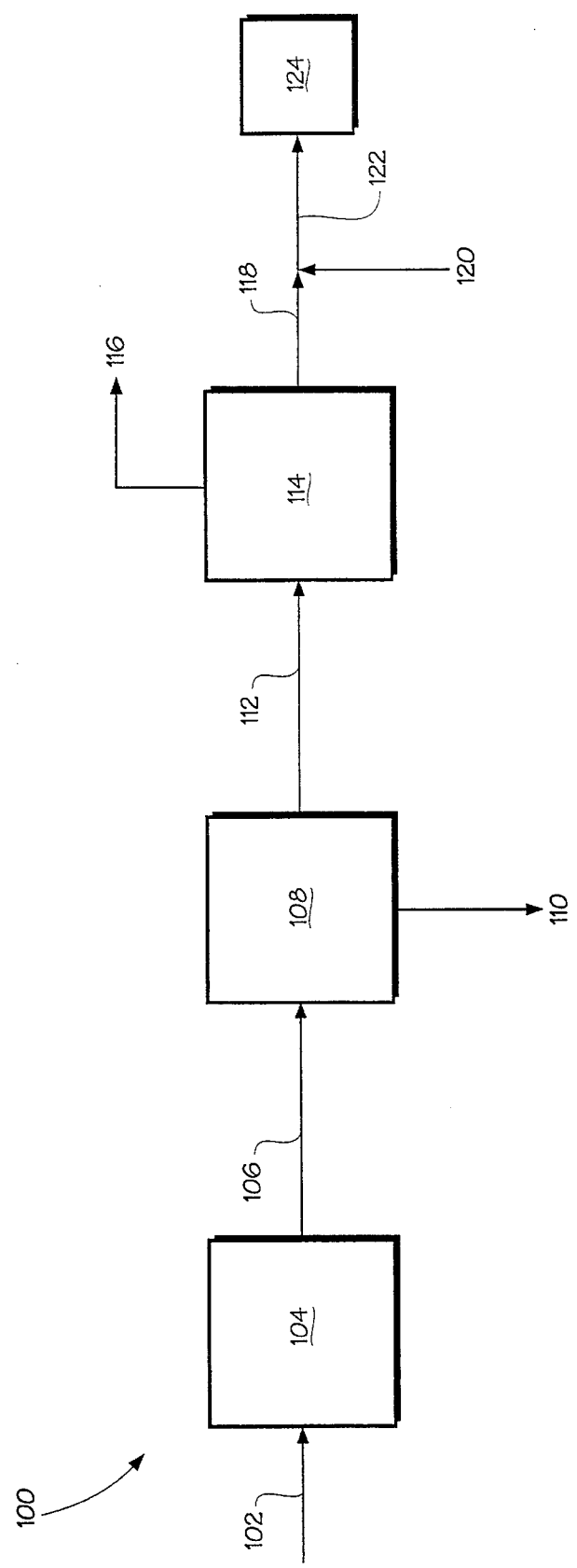
FIG. 3 is a flow diagram of another alternate embodiment of the present invention.

Referring to FIG. 3, another alternate process for recovering DMT 100 is shown.

Waste stream 102 is fed into methanolysis reactor 104 where DMT stream 106 is formed. DMT stream 106 contains DMT, methanol, glycols, catalysts, and coordination compounds. DMT stream 106 is fed into DMT separator 108, e.g. a centrifuge, as is well known in the art. In separator 108, DMT 110 and stream 112 are formed. Stream 112 generally contains glycols, methanol, catalysts, and coordination compounds.

Stream 112 is fed into methanol separator 114 to form methanol stream 116 and stream 118. Methanol separator 114 is any conventional process, which is well within the skill of the art. Stream 118 generally contains glycols, catalysts, and coordination compounds. Stream 118 is treated with acid stream 120 to disassociate the coordination compounds and forms stream 122. Stream 122 generally contains glycols, catalysts, and ligands. Stream 122 is fed into a conventional separator 124 to resolve the components of that stream.

The terms used to describe the invention are discussed below.

Waste stream refers to a process stream containing scrap polyethylene terephthalate (PET) or PET production waste or the product of a glycolysis reactor or combinations thereof. The source of the waste stream is not critical. PET production waste may be from the ethylene glycol recovery unit associated with the polycondensation step of the PET polymerization process (generally comprising about 70–30% by weight BHET/oligomer and about 30–70% by weight EG). BHET is the monomer that forms PET. Oligomers are short chain or low molecular weight polymers formed from BHET.

Methanolysis refers to the reaction by which the waste stream is converted into dimethyl terephthalate (DMT). Methanolysis involves the reaction of PET and/or BHET/oligomers with methanol to form DMT. Methanolysis is well known, e.g., see: U.S. Pat. Nos. 2,884,443; 3,037,050; 3,148,208; 3,321,510; 3,488,298; 3,907,868; 4,163,860; 4,578,502; and 5,051,528 each of which is incorporated herein by reference. Methanol refers to a methanol stream having greater than about 0.5% by weight water. The presence of water during methanolysis causes, as a side reaction, the formation of monomethyl terephthalate (MMT) and/or terephthalatic acid (TA). MMT and TA become ligands of the coordination compounds (discussed below).

DMT stream or dimethyl terephthalate stream refers to the product or the process stream exiting the methanolysis reaction. The DMT stream generally comprises: DMT; glycols; catalysts; and coordination compounds. The DMT stream may comprise, by weight, about 40–70% DMT, about 60–30% glycols, and about 0–3% catalysts. Preferably, the stream comprises about 60% DMT, about 40% EG, and about 1% catalyst. The DMT stream, preferably, should contain no more than about 2% by weight methanol, but greater amounts can be tolerated. If, after methanalysis, the DMT stream contains excess methanol, it should be removed in any known fashion.

DMT or dimethyl terephthalate also includes partially reacted products from the methanolysis reaction. Glycols refer to ethylene glycol (EG), diethylene glycol (DEG), triethylene glycol (TEG) and other higher glycols. EG is the principal glycol. Catalysts principally refers to the polycondensation catalysts from the PET polymerization, but it may also include catalysts from the methanolysis (e.g., transesterification catalysts). The catalysts are, most likely but not necessarily, antimony (Sb)—based, manganese (Mn)—based, titanium (Ti)—based, and/or germanium (Ge)—based catalysts.

Coordination compounds (also known as complex compounds) are formed by the union of a metal ion with a monometallic ion or molecule called a ligand or complexing agent. The catalysts are the source of the metal ions. The ligands, as discussed above, are produced in the methanolysis reaction.

Extractor refers to a process by which DMT is separated from the DMT stream. This process is a liquid-liquid or solvent extraction process. Operation of the extractor is known. See: U.S. Pat. No. 5,414,106 incorporated herein by reference. Solvent, when used in conjunction with the extractor, refers to any solvent that is immiscible with water and miscible with DMT. This solvent is preferably an organic solvent. Exemplary solvents include: methylbenzoate; xylene; toluene; and methyl-p-toluate. Water refers to any chemical process water stream.

Acid stream or acid refers to any acid (strong or weak acid) that is used to disassociate the coordination compounds into metals and ligands. Strong acids are preferred. Acids that may be used are selected from the group consisting of: phosphoric, sulfuric; hydrochloric; and acetic; and combinations thereof. Sulfuric acid is preferred. The amount of acid necessary to disassociate the coordination compound is illustrated by the following example: A stream containing about 0.0038 moles MMT and 0.0009 moles TA at a pH of 4.8 was titrated with 0.0044 moles of phosphoric acid ($H_3PO_4$). It is assumed that coordination compound has 3 MMT/metal ion. After titration, the solution had a pH of 2.5 and a white precipitate had formed.

Aqueous phase generally refers to the process stream from the extractor that contains, at least, water, glycols, and catalysts (metals). Organic phase generally refers to the process stream from the extractor that contains, at least, solvent, and DMT, but it may include ligands.

Organic phase separator refers to any unit operation for separating the solvent from the DMT and the ligands. Such unit operations are within the ordinary skill in the art.

Base stream refers to any base that is used to precipitate suspended metals from the aqueous stream. An exemplary base is potassium hydroxide (KOH). The amount of base needed to precipitate the suspended metals is illustrated by the following example: The filtrate from the foregoing example (pH-2.5) was basified with 1N KOH to pH-11. At pH-5, a pink solid (9.3% Mn and 4125 ppm Sb) began precipitating.

Filter refers to any unit operation for separating metals from the water and the glycols. For example, a centrifuge may be used.

The present invention may be embodied in other specific forms without departing from the spirit or essential attributes thereof and, accordingly, reference should be made to the appended claims, rather than to the foregoing specification, as indicating the scope of the invention.

We claim:

1. A process for recovering dimethyl terephthalate comprising the steps of:

a) providing a dimethyl terephthalate stream including dimethyl terephthalate, glycols, and coordination compounds;

b) acidifying the coordination compounds to disassociate ligands from metal ions;

c) separating the ligands from metal ions;

d) separating the dimethyl terephthalate from the glycols; and e) recovering the dimethyl terephthalate.

2. The process according to claim 1 further comprising the steps of:

basifying the metal ions stream to precipitate metal; and recovering said metal.

3. The process according to claim 1 further comprising: simultaneously performing steps b, c, and d.

4. The process according to claim 3 further comprising: separating the dimethyl terephthalate and the ligands from the glycols.

5. The process according to claim 1 further comprising: performing step d prior to step b.

6. The process according to claim 1 further comprising: performing step e prior to step b.

* * * * *